United States Patent [19]

Ramstack

[11] Patent Number: 4,769,150

[45] Date of Patent: Sep. 6, 1988

[54] METHOD AND APPARATUS FOR PLASMAPHERESIS BY RECIPROCATORY PULSATILE FILTRATION

[75] Inventor: Joseph M. Ramstack, West Chester, Pa.

[73] Assignee: E. I. Du Pont De Nemours and Company, Wilmington, Del.

[21] Appl. No.: 885,395

[22] Filed: Jul. 18, 1986

Related U.S. Application Data

[63] Continuation of Ser. No. 349,367, Feb. 16, 1982, abandoned.

[51] Int. Cl.[4] .............................................. B01D 13/00
[52] U.S. Cl. ................... 210/636; 210/651; 210/195.2; 210/321.69; 210/409
[58] Field of Search ............. 210/927, 433.2, 409, 210/636, 321.1, 651, 195.2, 321.69; 422/48; 604/4, 5, 6

[56] References Cited

U.S. PATENT DOCUMENTS

| | | | |
|---|---|---|---|
| 3,211,645 | 10/1965 | Ferrari | 210/22 |
| 3,212,642 | 10/1965 | Kylstra | 210/321 |
| 3,354,618 | 11/1967 | Dounoucos | 55/158 |
| 3,429,757 | 2/1969 | Nash | 156/70 |
| 3,541,005 | 11/1970 | Strathmann et al. | 210/19 |
| 3,684,097 | 8/1972 | Mathewson, Jr. et al. | 210/321 |
| 3,705,100 | 12/1972 | Blatt et al. | 210/23 |
| 3,966,616 | 6/1976 | Bray | 210/433 |
| 3,974,068 | 8/1976 | Ebner et al. | 210/650 X |
| 4,001,117 | 1/1977 | Trechsel | 210/180 |
| 4,075,091 | 2/1978 | Bellhouse | 210/19 |
| 4,191,182 | 3/1980 | Popovich et al. | 128/214 |
| 4,212,742 | 7/1980 | Solomon et al. | 210/247 |
| 4,411,792 | 10/1983 | Babb | 210/195.2 X |
| 4,579,662 | 4/1986 | Jonsson | 210/636 |

FOREIGN PATENT DOCUMENTS

| | | |
|---|---|---|
| 2653875 | 6/1978 | Fed. Rep. of Germany . |
| 2925143 | 1/1981 | Fed. Rep. of Germany . |
| 167009 | 12/1980 | Japan . |
| 01043 | 5/1980 | PCT Int'l Appl. . |
| 1555389 | 11/1979 | United Kingdom . |
| 2037614A | 7/1980 | United Kingdom . |
| 2048114A | 12/1980 | United Kingdom . |

OTHER PUBLICATIONS

Strathmann, *Journal of Membrane Science*, 9, (1981), pp. 121-189.

Dorson et al., Chem. Eng. Prog. Symp. Ser. 64, 9-1968, pp. 85-89.

Driscoll et al., Trans. Amer. Soc. Artif. Int. Organs XXIII, 6-1977, pp. 470-478.

Bixler et al., Trans. Amer. Soc. Artif. Int. Organs XIV, 6-1968, pp. 99-108.

*Primary Examiner*—Frank Spear

[57] ABSTRACT

Blood is oscillated between an inlet and an outlet of a flow path on a membrane during plasmapheresis by filtration.

16 Claims, 9 Drawing Sheets

F I G. 11
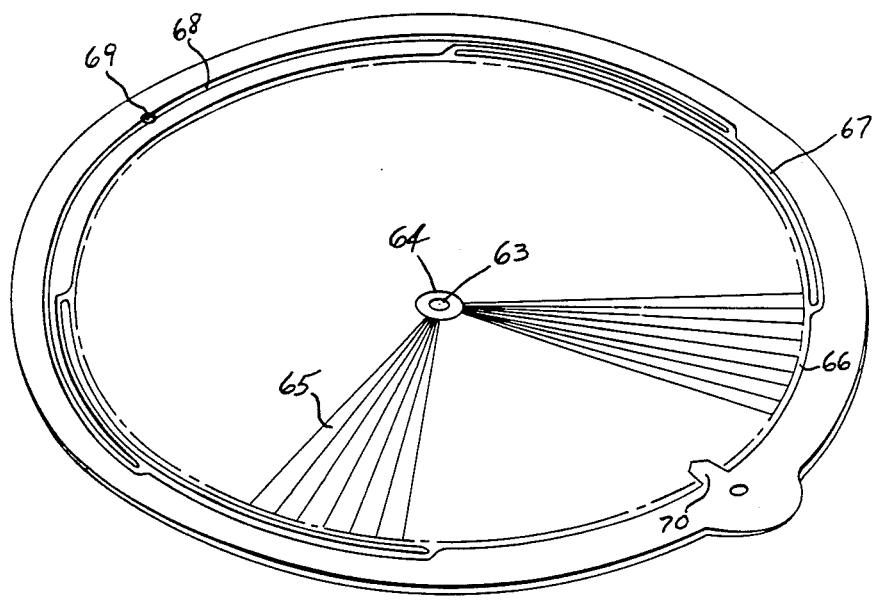
F I G. 12
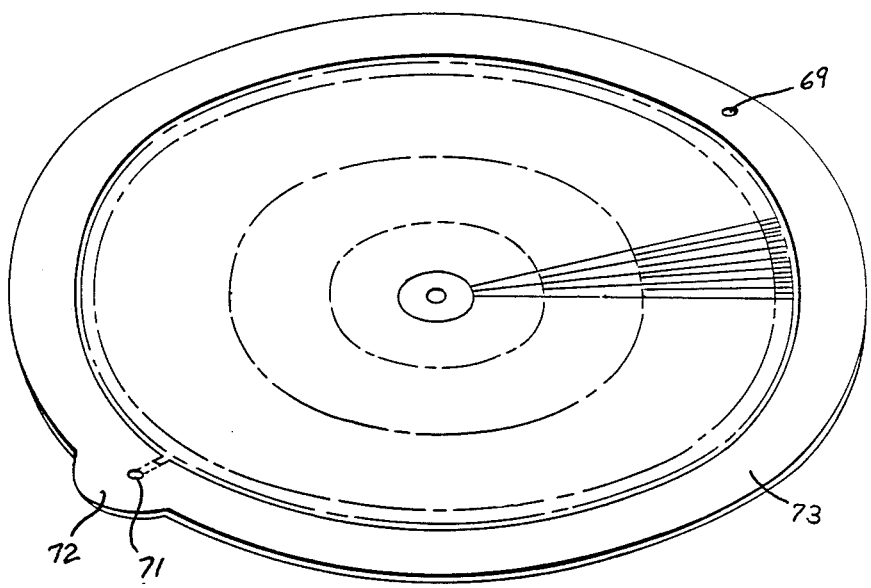

METHOD AND APPARATUS FOR PLASMAPHERESIS BY RECIPROCATORY PULSATILE FILTRATION

This is a continuation of application Ser. No. 349,367 filed Feb. 16, 1982 and now abandoned. Related subject matter is disclosed and claimed in application Ser. No. 009,003, filed Jan. 28, 1987, now U.S. Pat. No. 4,735,726, as a continuation of application Ser. No. 478,812, filed Mar. 30, 1983, now abandoned.

FIELD OF THE INVENTION

This invention relates to plasmapheresis by filtration and, more particularly, to a method and apparatus for imparting reciprocatory pulsations to blood in a blood flow path on a membrane surface during plasmapheresis.

BACKGROUND INFORMATION

Plasmapheresis is a process of separating plasma from whole blood. The plasma-depleted blood is comprised principally of cellular components, e.g., red blood cells, white blood cells and platelets. Plasma is comprised largely of water, but also contains proteins and various other noncellular compounds, both organic and inorganic.

Continuous plasmapheresis is the process of continuously removing whole blood from a subject, separating plasma from the blood and returning the plasma-depleted blood to the subject in a continuous extracorporeal circuit.

Plasmapheresis is currently used to obtain plasma for various transfusion needs, e.g., preparation of fresh-frozen plasma, for subsequent fractionation to obtain specific proteins such as serum albumin, to produce cell culture media, and for disease therapies involving either the replacement of plasma or removal of specific disease-contributing factors from the plasma.

Plasmapheresis can be carried out by centrifugation or by filtration. Generally, in known filtration apparatus, whole blood is conducted in a laminar flow path across one surface, i.e., the blood side surface, of a microporous membrane with a positive transmembrane pressure difference. Useful microporous membranes have pores which substantially retain the cellular components of blood but allow plasma to pass through. Such pores are referred to herein as cell-retaining pores. Typically, cell-retaining pore diameters are 0.1 $\mu$m to 1.0 $\mu$m.

Various filtration devices for plasmapheresis are disclosed in the literature. U.S. Pat. No. 3,705,100 discloses a center-fed circular membrane having a spiral flow path. U.S. Pat. No. 4,212,742 discloses a device having divergent flow channels. German Pat. No. 2,925,143 discloses a filtration apparatus having parallel blood flow paths on one side of a membrane and parallel plasma flow paths, which are perpendicular to the blood flow paths, on the opposite surface of the membrane. U.K. Patent Application No. 2,037,614 discloses a rectilinear double-membrane envelope in which the membranes are sealed together at the ends of the blood flow path. U.K. Patent Specification No. 1,555,389 discloses a circular, center-fed, double-membrane envelope in which the membranes are sealed around their peripheries. German Pat. No. 2,653,875 discloses a circular, center-fed double-membrane device in which blood flows through slot-shaped filter chambers.

It is an object of this invention to provide a method for imparting reciprocatory pulsations to blood in a blood flow path during plasmapheresis by filtration and an improvement in a filtration module for plasmapheresis by reciprocatory pulsatile filtration.

BRIEF DESCRIPTION OF THE DRAWINGS

FIG. 11 is a perspective view of an alternative blood side support which may be used in the invention.

FIG. 12 is a perspective view of an alternative plasma side support which may be used with the blood side support of FIG. 11.

DESCRIPTION OF THE INVENTION

Figure 1:
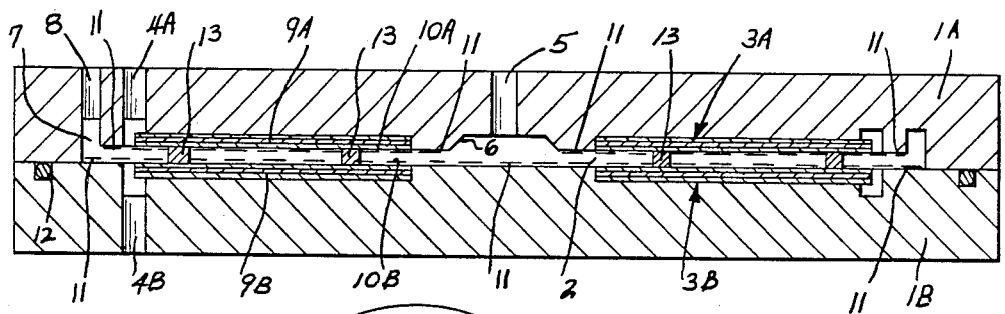
FIG. 1 is a cross-section of a double-membrane filtration module which may be used in the process of the invention, taken along line I—I of FIG. 2.

For further comprehension of the invention and of the preferred embodiments thereof, reference may be had to the following description and to the appended claims in which the various novel features of the invention are more particularly set forth.

The invention resides in a method for imparting reciprocatory pulsations to blood in a blood flow path on a surface of a membrane which comprises oscillating the blood between an inlet and an outlet. The invention also resides in said method which comprises superimposing oscillatory flow on a continuous forward flow of the blood and in the particular method which comprises oscillating the blood in a circuit which includes the blood flow path and a loop extending between an inlet and an outlet of the flow path.

The invention also resides in an improved plasmapheresis filtration module having a blood flow path on a surface of a membrane wherein the improvement comprises means for oscillating blood between an inlet and an outlet of the flow path, and also means for superimposing oscillatory flow on a continuous forward flow of the blood. A particular apparatus includes a circuit which includes the flow path and a loop extending between an inlet and an outlet of the flow path, the loop being provided with oscillating means. The module may be of any suitable shape or configuration.

In the description and examples of the invention which follow, the term "forward" is used to indicate a direction generally away from the source of blood; "reverse" indicates a direction generally towards the source of blood. Transmembrane pressure difference is determined by subtracting the pressure on the plasma side, i.e., the second surface of the membrane, from the pressure on the blood side, i.e., the first surface of the membrane. "Cell-retaining pores" means pores which substantially retain cellular components but allow plasma to pass through the membrane.

Plasmapheresis by filtration is enhanced by the use of fouling-reducing techniques, e.g., pulsatile flow, reciprocatory pulsatile flow and high blood flow rate via recirculation. Plasmapheresis using reciprocatory pulsatile flow, which is the invention of one other than the inventor herein, comprises the steps of:

(1) conducting blood in a forward direction over a first surface, i.e., a blood side surface, of each of one or more membranes having cell-retaining pores;

(2) terminating the forward conducting of blood over the first surface of each membrane;

(3) conducting the blood in the reverse direction over said first surface, the volume of blood flowed in the reverse direction being less than the volume of blood flowed in the forward direction in step (1);

(4) repeating steps (1)–(3) in sequence and collecting plasma which passes through each membrane from a second surface, i.e., a plasma side surface, thereof and collecting plasma-depleted blood from said first surface.

Other steps may also be included, e.g., recycling the plasma-depleted blood, treating plasma during filtration, diluting the blood with a compatible fluid and measuring various biologically significant factors.

From the location at which the blood first contacts the membrane, which may or may not be near a point on an edge or end of the membrane, blood is conducted in a forward direction in one or more flow paths. A flow path is the space through which the blood flows on the first surface of the membrane. Typically the depth of blood in each flow path is less than about 30 mils (0.76 mm).

Plasma is driven through the cell-retaining pores in the membrane by a positive transmembrane pressure difference. Typically, positive transmembrane pressure difference is generated primarily by resistance to forward blood flow, but it can also be generated in other ways, e.g., by decreasing pressure on the plasma on the second surface.

The amount of transmembrane pressure difference that can be withstood by blood without hemolysis is largely a function of cell-retaining pore size which is, typically, 0.1 to 1.0 $\mu$m, diameter. For most purposes, the preferred pore diameter is about 0.4 to 0.6 $\mu$m. In this range, a positive transmembrane pressure difference of no more than about 4 psi (28 kPA) is desirable. When the pore diameter is smaller or larger, higher or lower transmembrane pressure differences, respectively, are acceptable, although it is preferred that the transmembrane pressure difference be kept low, e.g., below about 1.5 psi (6 kPa).

After the forward conducting of blood, the blood is conducted in the reverse direction in each flow path. The frequency and volume of the reciprocatory pulses are selected to maximize the flow of plasma through the membrane without causing extensive blood trauma. In a blood flow path having a height of about 4 to 10 mils (102 to 254 $\mu$m), a useful frequency and volume are about 20 to 140 pulsations per minute and 0.5 to 4 mL per pulsation, preferably about 3 mL. Said parameters should be selected to provide a mean linear velocity up to about 400 mm-sec$^{-1}$, preferably, up to about 250 mm-sec$^{-1}$. The net volume of blood flowed in the reverse direction is less than the net volume of blood flowed forward.

The blood which approaches the ends of each flow path is plasma-depleted blood. It is collected and conducted away from the membrane by any suitable means, as is the plasma which flows through the membrane.

Any type of useful membrane(s) in any suitable shape, configuration or arrangement, including, e.g., hollow fibers, can be used. Similarly, any suitable means can be used to conduct blood to the membrane and plasma-depleted blood and plasma from the membrane.

Referring to FIG. 1, a useful filtration module, which is the invention of one other than the inventor herein, comprises two circular opposing module housing plates 1A, 1B which are prepared from a blood-compatible material. A circular blood flow region 2 is recessed within an opposing surface of one or both plates. Further recessed within each plate is a plasma flow region 3A, 3B. Typically, though not necessarily, the plasma flow region is of smaller diameter than the blood flow region.

The depth of the plasma flow region is typically about 5 to 20 mils (127 to 508 $\mu$m). The surface of the plasma flow region may be smooth or grooved to enhance radial flow of plasma. In the plasma flow region, or connected thereto, may be means for treating the plasma for the removal of disease-contributing factors One or both plates 1A, 1B have plasma outlet ports 4A, 4B connected to the plasma flow regions 3A, 3B via a plasma collection channel around the plasma flow region, e.g., about 3 mm deep and 1.5 mm wide. There may be one or more of such ports in either or both plates. The ports and channel may be located at any position but preferably, as herein illustrated, are located near the periphery of each plasma flow region.

Near the center of plate 1A is blood inlet port 5, the walls 6 of which extend through plasma flow region 3A to the blood flow region 2. Around the periphery of blood flow region 2 is a plasma-depleted blood collection channel 7. This channel connects to one or more plasma-depleted blood outlet ports 8.

Within each plasma flow region is plasma side membrane support 9A, 9B which may be, e.g., a plate having grooves, pores or projections or fabric-like materials. The plasma side supports in the Figure are comprised of layers of fabric-like materials, such as layers of a nonwoven polyester fabric, such as Hollytex made by calendering Du Pont Reemay ® spunbonded polyester. This support provides adequate support while allowing transverse and radial flow of plasma. Support 9A which fits in plasma flow region 3A is provided with an aperture which fits around the wall 6 of blood inlet port 5.

Within each blood flow region is membrane 10A, 10B. Each membrane is made of a blood-compatible material and has cell-retaining pores. Such pores are typically about 0.1 to 1.0 $\mu$m average diameter. The selection of pore size may vary with the goal of a particular treatment. Useful membranes are described in some of the above-cited references relating to plasmapheresis. Membrane 10A which fits in blood flow region 2 is provided with an aperture which lies in registry with blood inlet port 5.

Membranes 10A, 10B are adhered to the plates near the peripheral edges of the membranes and, in the case of the membrane 10A, near the edge of the aperture which is in registry with blood inlet port 5, with an elastomeric adhesive. The areas of the plates 1A, 1B to which membranes 10A, 10B are adhered are identified in FIG. 1 by the number 11.

It has been found that when thin polycarbonate or polyester membranes which have low break elongation, i.e., less than about 40%, are employed in filter modules in which, as herein illustrated, the membranes are not rigidly supported across a large part of their surface areas, it is advantageous to employ an elastomeric seal between the membranes and supports. Use of an elastomeric seal provides sufficient flexibility to avoid rupture of the membranes during use. When such membranes are employed, the seal preferably has a break elongation of at least about 100%. The optimal break elongation will depend on several factors which will be obvious to persons skilled in the art, including the thickness of the seal. An elastomeric seal which has been found to perform well with such membranes is an adhesive having a break elongation of about 400% and applied in a layer about 3 mils (76 μm) thick. This is the invention of one other than the inventor herein.

When the module is assembled, the corresponding flow regions of each plate are adjacent. The plates are held together by any suitable means, e.g., clamps, bolts and adhesives. O-ring 12 can be used to seal the plates. The region between the membranes is the blood flow path. The total effective surface area of the membranes, i.e., the sum of the areas on both membranes over which blood can flow, is typically about 0.02 to 0.06 m².

Blood side supports 13 are located between the membranes. Blood side supports, though not necessary, have been found to be particularly useful when nonrigid plasma side supports, such as layers of Hollytex, which may tend to buckle during use, are employed. Various suitable supports are described in the literature. The illustrated supports comprise a plurality of smooth pillars, e.g., substantially circular, dots of a material which has sufficient softness to avoid breakage of the membranes during use, such as an elastomeric adhesive. Conveniently, the same adhesive which is used to adhere the membranes to the plates can be used to form the blood side supports.

Figure 2:
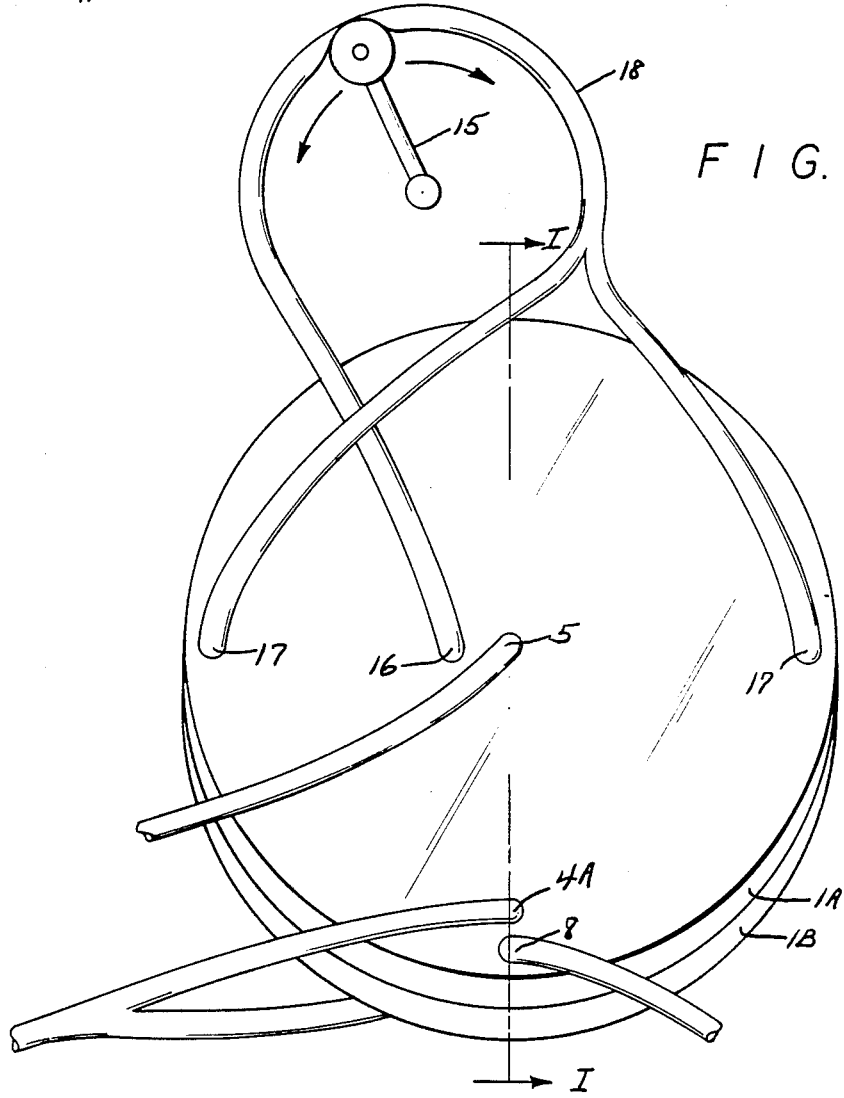
FIG. 2 is a perspective view of an illustrative embodiment of the filtration module of FIG. 1 having a loop and an oscillator to oscillate blood in a blood flow path between inlet and outlet.

FIG. 2 is an illustration of an embodiment of the invention employing the filtration module of FIG. 1. Blood is conducted from the source to the blood flow path via blood inlet port 5 in module housing plate 1A. Plasma which passes through the membranes exits from the module through plasma outlet port 4A, and a second plasma outlet port, not shown. Plasma-depleted blood from the end of the blood flow path exits from the module through plasma-depleted blood outlet port 8. In addition, blood flow is pulsed in reciprocatory fashion by peristaltic oscillator 15, which is connected to central and peripheral ports 16 and 17 through loop 18, which peripheral ports are connected to areas near an end of the flow path, directly, or indirectly via a blood collection channel, not shown. The loop is preferably short so that blood in the loop is frequently mixed and exchanged with blood in the flow path. There preferably is little or no exchange of blood across the oscillator. Any suitable type of pump may be used to cause the reciprocatory pulsations. Such pumps are described in the literature and in the Examples below; a peristaltic pump is preferred. Preferably, though not necessarily, the oscillator is connected to the blood flow path via one centrally located port 16 and two peripherally located ports 17, as shown, that is to the blood inlet and plasma-depleted blood outlet lines at a location close to the module. The duration and frequency of oscillations can be regulated by adjusting the oscillator. The forward and reverse strokes are typically of equal volume.

Figure 3:
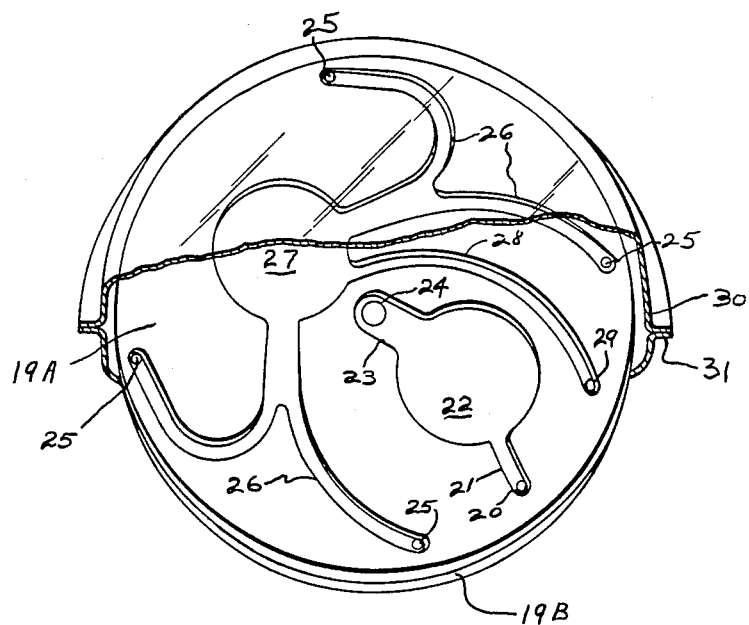
FIG. 3 is a perspective view of a module having an end plate which has reciprocatory pulse cavities.

FIG. 3 illustrates a partially exploded view of a module having an end plate, i.e., module housing plate, which has reciprocatory pulse cavities integral therewith. The end plate is the invention of one other than the inventor herein.

Blood is conducted into the module via a module inlet, not shown, in end plate 19B and is conducted through a matched port 20 in end plate 19A. From port 20 in end plate 19A, the blood is conducted through shallow channel 21, 0.2 inch (5.1 mm) wide × 0.06 inch (1.5 mm) deep, into inlet reciprocatory pulse cavity 22 which has a volume of about 3 mL and is about 2 inches (50.8 mm) in diameter × 0.06 inch (1.5 mm) deep. Cavity 22 is employed in the generation of reciprocatory pulsations as described below. From cavity 22, the blood is conducted through shallow channel 23, 0.5 inch (127 mm) wide × 0.13 inch (3.3 mm) deep, to blood flow path inlet 24 which is about 0.38 inch (9.7 mm) in diameter, i.e., cavity 22 is between module inlet 20 and blood flow path inlet 24. The blood is conducted through port 24 into a blood flow region between two membranes as described above. Plasma-depleted blood is conducted through flow path outlets 25 and through branch channels 26 to outlet reciprocatory pulse cavity 27 in end plate 19A. The branch channels from the four outlets 25, which are equidistant from each other, begin as four channels each about 0.250 inch (6.4 mm) wide × 0.060 inch (1.5 mm) deep and merge into two channels each about 0.500 inch (12.7 mm) wide × 0.060 inch (1.5 mm) deep. The branch channels are of equal length and cross-section so as to produce substantially equal pressure conditions during use. Cavity 27 is also employed in the generation of reciprocatory pulsations as described below. From cavity 27, the plasma-depleted blood is conducted through shallow channel 28, 0.200 inch (5.1 mm) wide × 0.060 inch (1.5 mm) deep, and through plasma depleted blood outlet 29 which extends through a matched port in end plate 19B, i.e., cavity 27 is between blood flow path outlets 25 and module plasma-depleted blood outlet 29.

Plasma which passes through the membranes flows radially in a plasma flow path and through a plasma collection channel, as described above, to an outlet port, not shown, in end plate 19B.

The entire module is enclosed by envelope 30, which is cut away in the illustration. It is comprised of two sheets of a flexible blood impermeable material, such as poly(vinyl chloride), the sheets being joined together at seal 31 around the perimeter of the stack. The envelope thus provides a unitary flexible enclosure for the module. The three apertures in end plate 19B mate with tube connectors in envelope 30. The above modules must be clamped using pressure which is at least sufficient to offset internal pressure. In the examples below, a series of c-clamps around the perimeter of each module was employed.

Figure 10:
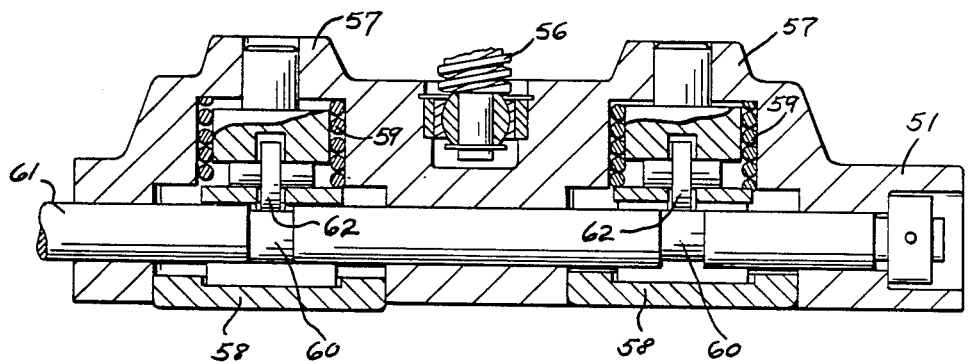
FIG. 10 is an elevational view in cross-section of a pumping arrangement used with the module of FIG. 4.

Envelope 30 covers and seals the various channels, cavities and apertures in end plate 19A and forms a flexible diaphragm over each cavity 22, 27. A perimeter lip, not shown, around each cavity and channel in end plate 19A aids in sealing. Reciprocatory pulsations are generated by alternately compressing the diaphragm over each cavity 22, 27 such as by the use of reciprocating plungers. Reciprocating plungers which are useful for this purpurse are illustrated by FIG. 10.

Figure 4:
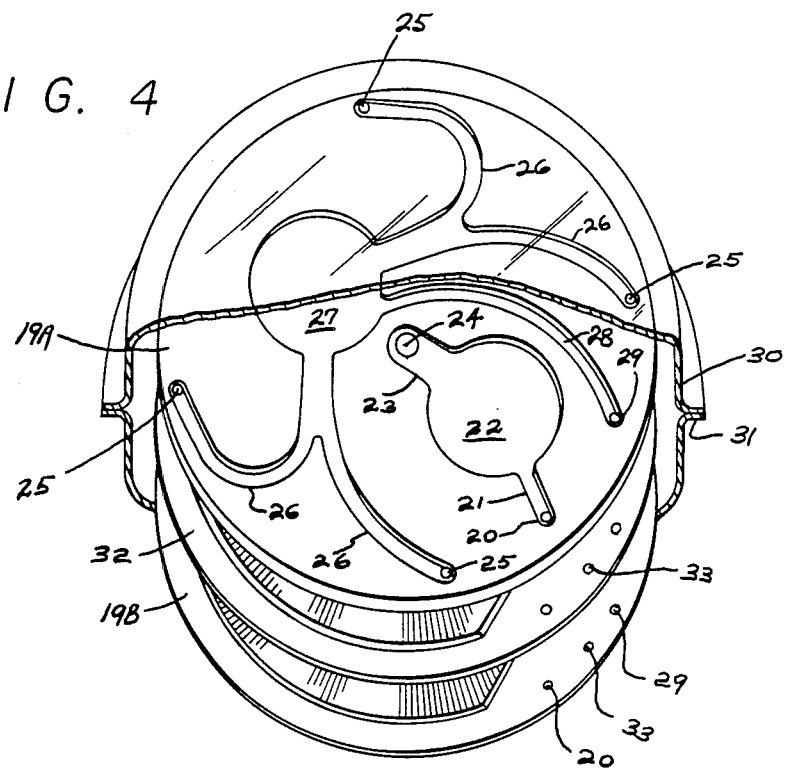
FIG. 4 is an exploded view of a module which is preferred for use in the invention.

FIG. 4 is illustrative of a two membrane filter module having an end plate as described above in FIG. 3. The module and end plate are the inventions of ones other than the inventor herein but are included herein because they are illustrative of a means for carrying out this invention and of the preferred module comprising said means. FIGS. 5 to 9 illustrate particular elements of the module of FIG. 4. Referring to FIG. 4, the module comprises a clampable stack of plates 19A, 19B, 32, between which, suitable membranes, not shown, are interleaved. The plates are flexible and require external structural support, such as is described below with reference to FIGS. 8 and 9, to effect sealing and to compensate for compliance and tolerance within the module. Blood is conducted into the module via inlet 20 in end plate 19B and is conducted through matched ports in plates 32, 19A. End plate 19A is about 0.19 inch (4.8 mm) thick; end plate 19B and plate 32 are about 0.08 inch (2.0 mm) thick; the module is about 8 inches (0.2 μm) in diameter.

Figure 5:
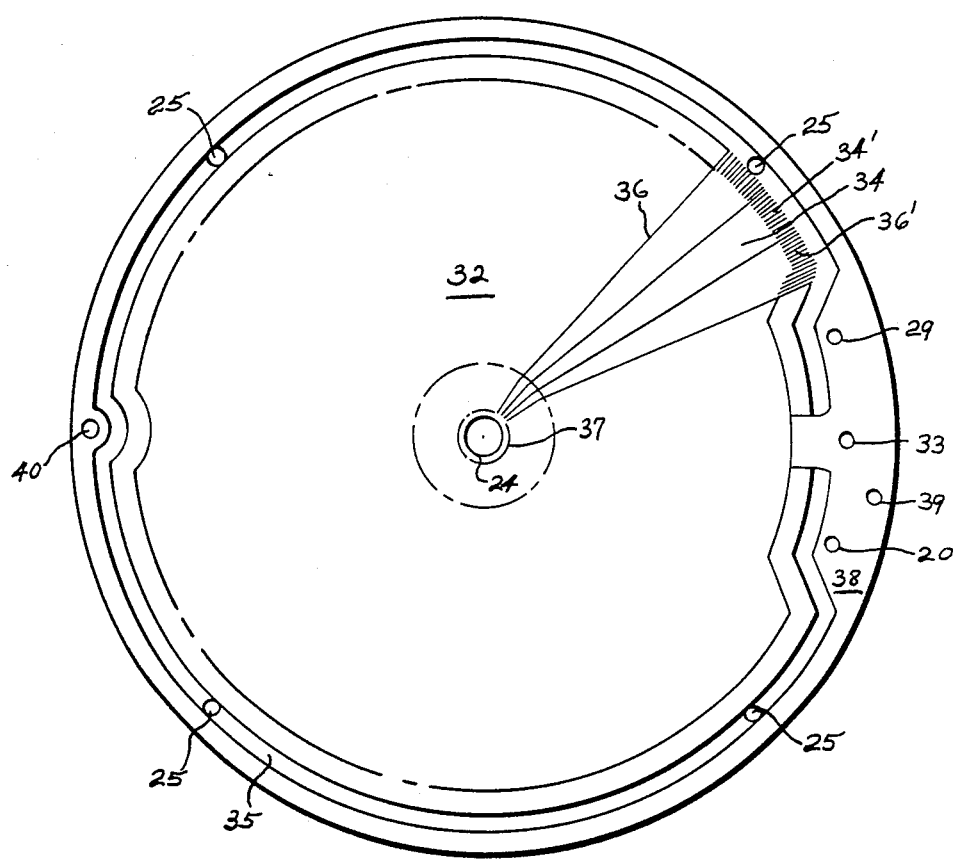
FIG. 5 is a plan view of a blood side support of the module of FIG. 4.

From module inlet 20 in end plate 19A, the blood is conducted to port 24, as described above in FIG. 3, and through matched ports in plates 32 and in the membranes, to blood flow paths lying between each membrane and one surface of a plate, e g, on a membrane lying between end plate 19A and adjacent plate 32, the blood flow path is between the membrane and the interior surface of end plate 39A, which is a blood side support, as illustrated for plate 32 in FIG. 5. The blood in the blood flow paths is conducted radially to plasma-depleted blood collection channels and from there, through matched flow path outlets 25 as described above in FIG. 3.

Figure 6:
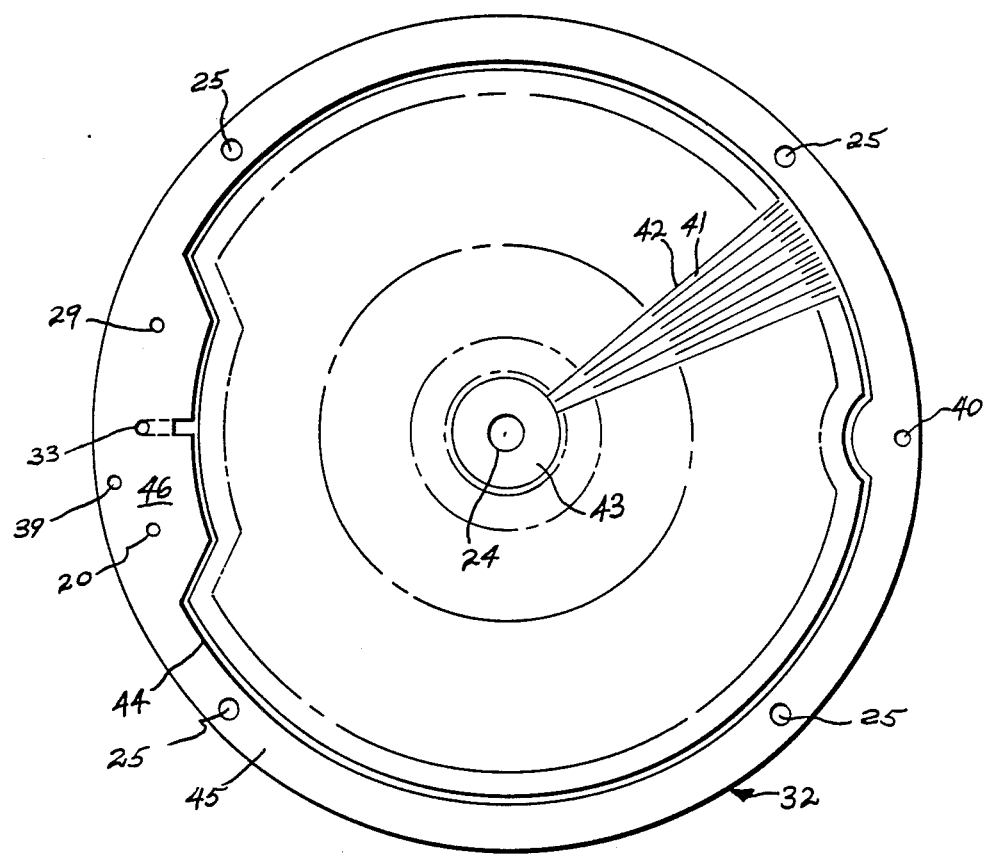
FIG. 6 is a plan view of a plasma side support of the module of FIG. 4.

Plasma which passes through the membranes flows radially in a plasma flow path, e.g., on the membrane which lies between end plate 19A and adjacent plate 32, the plasma flow path is between the membrane and plate 32. The plasma flow path is comprised of radial flow channels which culminate in a perimeter plasma collection channel, as illustrated by FIG. 6, from which the plasma pases through matched ports 33 in plates 32, 19B and out of the module. A section of plasma flow channels is illustrated in FIG. 4. The entire module is enclosed by envelope 30 as described above in FIG. 3.

FIG. 5 illustrates a blood side support comprised of plate 32, a surface of which is provided with recessed radial blood flow channels 34. Between channels 34 are ridges 36. The channels 34 extend from counterbore 37 around inlet 24. For purposes of illustration, only a portion of enlarged blood flow channels are shown. In fact, ninety channels 34 extend around the entire perimeter of inlet 24 although more or fewer channels may be employed. The channels 34 are at least about 4 mil (0.1 mm) deep, preferably about 4 to 10 mils (0.1 to 0.3 mm). They are narrow around the inlet and increase in width from about 8 mils (0.2 mm) to about 250 mils (6.4 mm). The counterbore is about 20 mils (0.5 mm) deep and 0.5 inch (12.7 mm) in diameter. Around the perimeter of flow channels 34 is perimeter plasma-depleted blood collection channel 35 which leads to plasma-depleted blood outlet ports 25. Between flow channels 34 and collection channel 35 are blood pressure balancing and sealing grooves comprising a perimeter border of short narrow channels 34', each about 4 to 30 mils (1. to 0.8 mm) wide. Between perimeter channels 34' are ridges 36'. Perimeter channels 34' enhance uniform distribution of pressure and flow within the blood flow channels by causing increased velocity and hence increased pressure drop across the perimeter channels.

In region 38, the channels are spaced inward from the edge of the plate so as to avoid intersecting any of ports 20, 33, 29. The channels 34 are offset from radial plasma flow channels on a plasma side support so that the ridges between the blood flow channels and the ridges between the plasma flow channels will not be contiguous but rather will intersect, thus minimizing the risk of membrane shearing; in the illustrated embodiment, approximately the outer 80% of the axes of flow channels 34 are angled slightly from a pure radial direction. Also to minimize the risk of shearing, the ridges between the channels preferably have flat surfaces, e.g., about 3 to 10 mils (0.1 to 0.3 mm) wide.

Alignment pins 39 and 40 fit snugly into aligned holes in each plate 19A, 19B, 32, thus maintaining the plates in the proper relative orientation.

The preferred plasma side support, opposite the blood side support, is illustrated by FIG. 6. The plasma side support comprises the other surface of plate 32, having plasma flow channels 41 recessed in one surface thereof with ridges 42 therebetween. The plasma flow channels 41 extend from a central sealing surface 43 in zones of progressively greater numbers to a perimeter plasma collection channel 44, which is about 0.07 inch (1.8 mm) wide×0.030 inch (0.8 mm) deep. For purposes of illustration, only a section of enlarged plasma flow channels are shown. By progressively increasing the numbers of plasma flow channels, closely-spaced ridges, which provide support for the membrane, are maintained. In the illustrated plasma side support, the number of plasma flow channels doubles in each succeeding zone so that in the innermost zone there are 90 such channels and in the outermost zone there are 1440 such channels.

In the center of plate 32 is a blood flow path inlet 24, e.g., about 0.39 inch (9.9 mm) in diameter, which is in registry with blood flow path inlet 24 in plate 19A.

The inlet sealing surface 43 is an area on the plasma side support which is coplanar with the nonrecessed areas of the support. It is opposite narrow blood flow channels on an opposing blood side support so that when the supports are pressed together with a membrane therebetween, blood is substantially prevented from leaking into plasma flow regions without the use of adhesives or gaskets. Surface 43 is a circular area, concentric with inlet 24 and of larger diameter, e.g., about 1 inch (25.4 mm). Preferably, it is an inlet sealing boss although other elements can be used, e.g., an annular insert. It substantially prevents blood from leaking from inlet 24 to plasma flow channels 41. The plasma collection channel 44 is located within a smaller radius than the short, narrow channels 34' on plate 19A. Between the plasma collection channel 44 and the edge of plate 32 is a perimeter sealing surface 45 which can be pressed against channels 34', there being a membrane therebetween, effecting a seal in a manner similar to the seal around inlet 24.

From the plasma collection channel 44, plasma flows to plasma outlet 33. As with the blood side support, the channels are spaced inward from the edge of the plate in region 46.

The interior surface of plate 19A in FIG. 4 also comprises a blood side support identical to that shown in FIG. 5. Several plates 32 can be stacked to permit use of a desired number of membranes, the preferred number being four to six. The last plate, i.e., end plate 19B, comprises a plasma side support, on its interior surface, which is identical to the plasma side support illustrated in FIG. 6 except that end plate 19B is not apertured with blood flow path inlet 24. On its exterior surface, end plate 19B is plain.

Figure 7:
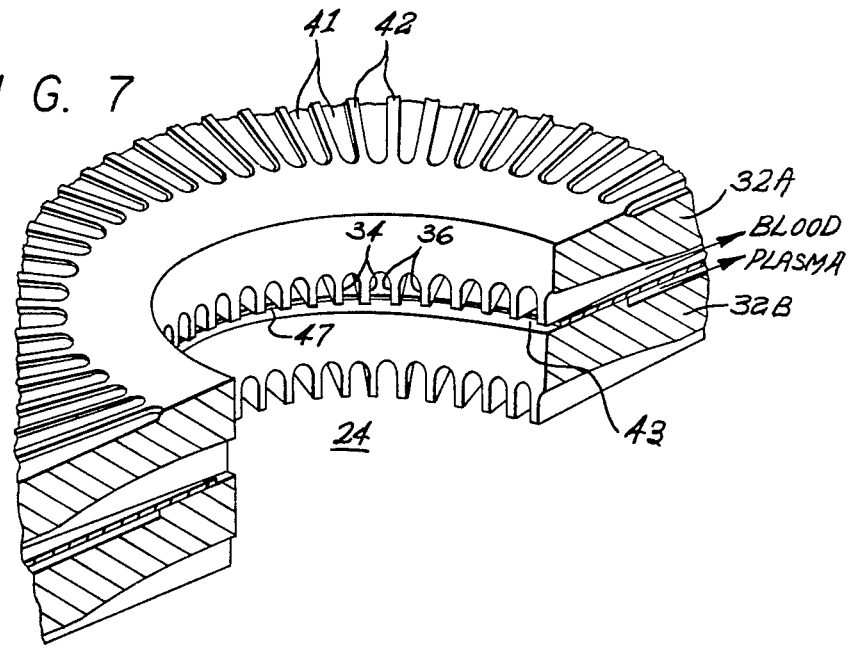
FIG. 7 is a cross-sectional view of a central sealing region in the module of FIG. 4.

FIG. 7 illustrates the central sealing designs of the module and the preferred blood flow path entrance design. The membrane 47 is pressed between the blood side support surface of one plate 32A and the plasma side support surface of a second plate 32B. In this figure, there is no counterbore around the inlet as there is in FIG. 5. Membrane 47 bridges the narrow blood flow channels around inlet 24 and is squeezed against central sealing boss 43 of the next plate, acting in this region as seal members in a manner similar to a check valve. By employing channels which are about 4 to 20 mils 0.1 to 0.5 mm), preferably 6 to 10 mils (0.2 to 0.3 mm), in width, under usual operating conditions, i.e., pressures up to about 3 psi (21 kPa), the membrane seal has been found to substantially prevent leakage of blood even when reciprocatory pulsatility is employed, when the module is pressed between clamp jaws.

As can be seen in FIG. 7, the entrance to each blood flow channel is initially deep but uniformly decreases in depth, as the flow channels widen, such that the cross-sectional area of each is substantially maintained while the depth is decreased. This design enhances uniform flow in the module and allows the flow conditions in the thin channels to be attained more gradually than if the entrances to the channels were also thin. The initial depth is greater than about 10 mils (0.3 mm), preferably about 15 to 20 mils (0.4 to 0.5 mm) and is gradually decreased to about 4 to 10 mils (0.1 to 0.3 mm).

Envelope 30 allows the module to be purged of air and filled with a liquid, e.g., saline, prior to use. When the module is used, this saline solution is swept out of the flow channels by blood and plasma but remains around the periphery of envelope 30 in the region of seal 31. Any blood which may leak into this solution in this region remains there by a check-valve action, due to the seal between perimeter channels 34' and the perimeter sealing boss 45 illustrated in FIGS. 5 and 6, similar to that described for the sealing region surrounding inlet 24 in FIG. 7.

Figure 8:
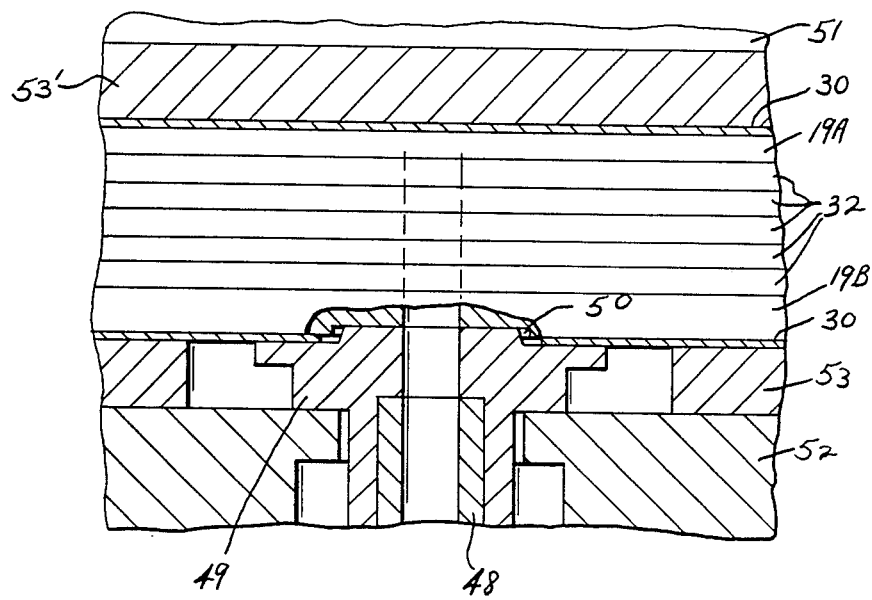
FIG. 8 is an elevational view in cross-section of the attachment of an inlet or outlet tube to the module of FIG. 4.

As shown in FIG. 8, tube 48 connections to the apertures 20, 33, 29 are made by joining flanged plastic fittings 49 to the plastic envelope 30 on the bottom of the unit as seen in FIG. 4. No direct connection is made to any of the plates 19B, 19A, 32; however, the fittings are urged against the envelope 30 and into shallow counterbores 50 in end plate 19B by means of a clamping mechanism, namely, jaws 51, 52. Counterbores 50 prevent the plates from moving relative to the envelope during use. Jaws 51, 52, faced with elastomer 53, 53', engage envelope 30 at the top of plate 19A and the bottom of plate 19B and, in addition to holding the tube fittings, urge the stacked plates together in leak-tight condition resisting the hydrostatic pressure of the blood being pumped through the module. Unit pressures within the module are in the order of 0.5 to 3 psi (3.4 to 20.7 kPa) on an area of 40 sq. in. (250 sq. mm) resulting in clamp loadings of 120 lb. (54.4×10³ gm). The clamp must provide sufficient external pressure to offset this internal pressure as well as to compensate for compliance and manufacturing tolerances. This external pressure should be evenly distributed.

Figure 9:
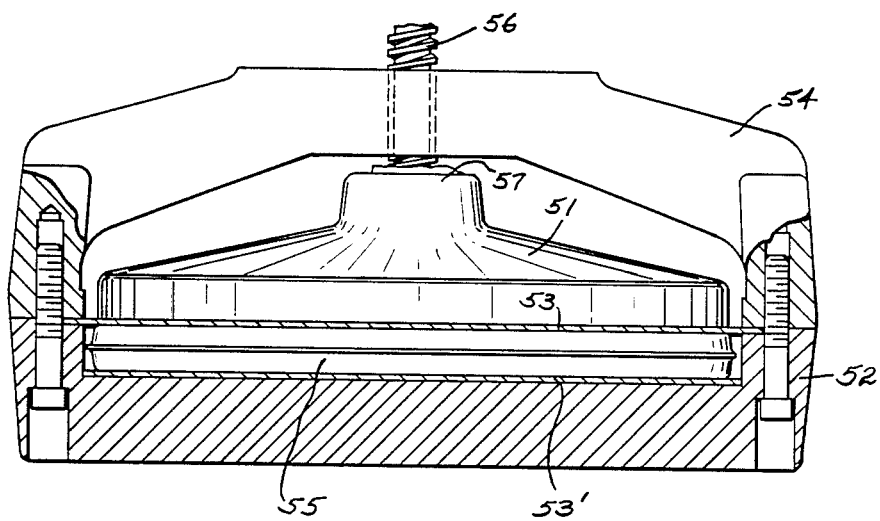
FIG. 9 is a cross-sectional view of a module of the invention pressed between clamp jaws.

Referring to FIG. 9, jaw 52 is a rectangular platen having yoke 54 bolted thereto. Yoke 53 has four legs, two shown; the number of legs is not critical. Jaw 51 is a floating and self-aligning circular platen of larger diameter than module 55 which is pressed against module 55 by means of central gear-reduced screw 56 extending through yoke 54 and connected to jaw 51 by means of a swivel joint, not shown. A gear-reducing mechanism, not shown, is fitted to the top of yoke 54. Two bosses 57, shown cut off, are on either side of screw 56 and house reciprocating plungers, as further described below with reference to FIG. 10. Elastomer 53, 53' lie between jaws 51, 52 and module 55. A guide pin, not shown, extending through yoke 54 to jaw 51 is used to properly align jaw 51 with module 55 upon clamping. It has been found that use of such a clamping mechanism provides nearly uniform pressure across the module and provides structural support external to the module, thereby lowering the cost of the module which is a disposable unit.

FIG. 10 illustrates the reciprocating plungers of a pulse generator integral with jaw 51. It is a cross section taken perpendicular to the cross section of FIG. 9. Jaw 51 has bosses 57 for two parallel bores occupied by plungers 58 which are shouldered to carry springs 59 which urge the plungers toward reciprocatory pulse cavities. The plungers are lifted 180° out of phase with each other by means of eccentrics 60 on a common shaft 61 which is carried in bearings, not shown, and is extended outside the bar for a belt connection to a motor drive not shown, which is mounted on brackets, not shown, extending from jaw 51. The eccentrics 60 each engage a roller 62 in a slot in each plunger 58. Each roller 62 is carried on a wrist pin in the plungers. The throw of the eccentrics is about 0.030 inch (0.8 mm) producing a plunger stroke of about 0.060 inch (1.6 mm). The eccentric shaft drives the pistons down away from the diaphragm compressing the springs and storing energy. The pistons are returned by the springs which limit the maximum force and resulting pressure which can be generated by the piston on the diaphragm over each cavity. This also limits jamming damage should the unit be installed misaligned or with a foreign body in the clamp cavity area.

The bottom of jaw 51 is pressed against plastic envelope 30 by the clamp so that the plunger heads 58 enter the reciprocatory pulse cavities. Rotation of shaft 61 causes diaphragm-like deflections in envelope 30 and produces a pumping action on fluids in the cavities. This action is oscillatory, causing recipricatory pulsatile flow on the surfaces of the membrane filters. Because the reciprocatory pulse cavities are integral with the modular assembly of stacked plates and filter membranes, there is minimal addition to the average hold-up time of the blood being processed and each flow fraction receives uniform treatment.

FIGS. 11 and 12 illustrate, respectively, an alternative blood side support and an alternative plasma side support which may be used in a module of the invention. The supports and module are the inventions of one other than the inventor herein. Referring to FIG. 11, at the center of the plate is blood flow channel inlet 63 surrounded by counterbore 64, which is about 0.5 inch (12.7 mm) in diameter and about 20 mils (0.5 mm) in depth. From the counterbore, radial flow channels 65, shown enlarged and in part, are narrow around the inlet and extend to a perimeter plasma-depleted blood collection channel which is a series of plasma-depleted blood collection channels 66, 67, 68. These channels lead to plasma-depleted blood outlet 69. In the illustration is shown a first perimeter channel 66 which has four equidistant exits to intermediate channels 67 each of which in turn have an exit to final channel 68. Each channel is about 0.070 (1.8 mm) wide×0.030 inch (0.8 mm) deep. These channels comprise blood pressure balancing and sealing grooves serving, in this regard, the same purpose as the perimeter border of short, narrow channels 34' in FIG. 5. The channels are spaced inward in region 70 to avoid plasma channels and ports.

FIG. 12 illustrates a plasma side support which may be used with the alternative blood side support of FIG. 11. It differs from the plasma side support described above in FIG. 6 in the locations of blood outlet 69 and plasma outlet 71, the latter of which is in a protrusion 72 from the edge of the plate in order to avoid the various blood flow channels and ports. Sealing around the inlet is accomplished as illustrated above in FIG. 7. Sealing around the perimeter is effected by a check-valve-like action resulting from pressing a membrane between channels 66, 67, 68 on the blood side support and perimeter sealing surface 73 on the plasma side support, in a manner similar, though not as effective, as described above with reference to FIG. 7.

Figure 13:
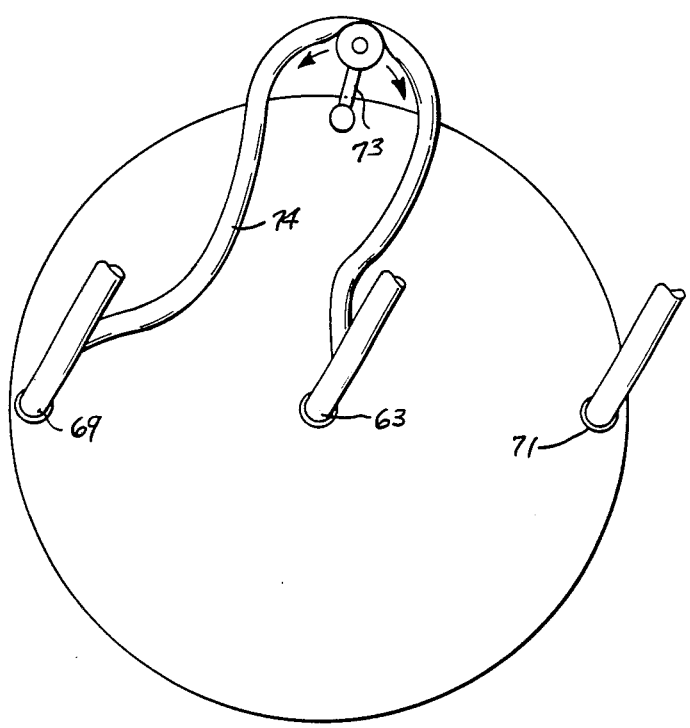
FIG. 13 is a plan view of a second illustrative embodiment of a module which is useful in the invention and can be used with the supports of FIGS. 11 and 12.

A second illustrative embodiment of a module, which can be used in the invention, employing the blood and plasma side supports of FIGS. 11 and 12, is shown in FIG. 13. This illustrative embodiment is not fitted with reciprocatory pulse cavities. Blood enters the module through blood flow path inlet 63, passes through blood flood flow channels, not shown, in blood side supports, not shown, and exits through plasma-depleted blood outlet 69. Plasma which passes through membranes between plasma and blood side supports flows radially to plasma collection channels and out of the module via plasma outlet 71. An external clamping mechanism, such as the mechanism described above, absent the pulse generator, is used to provide structural support.

Reciprocatory pulsations are generated by an oscillating peristaltic pump 73 on a loop 74 of flexible tubing extending between blood inlet 63 and plasma-depleted blood outlet 69. Pulse volume can be changed, e.g., by changing stroke length or the diameter of tubing used for the loop.

EXAMPLES 1 TO 3

In Examples 1 to 3, which are illustrative of single pass treatments to separate plasma from blood in a filtration module which is the invention of one other than the inventor herein and which is substantially illustrated in FIGS. 1 and 2, compatibility-matched human blood collected in ACD or heparin and maintained at 37° C. during treatment was used.

The membranes were polycarbonate capillary pore membranes, available from Nuclepore Corporation, having average cell-retaining pore diameters of about 0.4 μm, about 10% pore area and a break elongation of 10 to 15%, machine direction, and 25 to 30%, cross direction, and were about 10 μm thick. The plasma side supports comprised three layers of 4 mil (102 μm) thick Hollytex.

Prior to each treatment, the module was purged of air by flushing with saline. The Hollytex supports were first solvent-exchanged in isopropanol, soaked in saline and then placed wet in the membrane filter module. The membrane filter module was submerged in saline, 37° C., during treatment to prevent air leakage. Removing air from and maintaining air out of the module is important.

The blood side pressure was measured by means of pressure strain gauge transducers and monitored near the center (inlet) and/or near the periphery (outlet) of the blood flow path. The plasma side of the apparatus was vented and was assumed to be at atmospheric pressure.

Hemolysis was determined by visual observation of samples of plasma periodically collected during each treatment. The hematocrit (Hct.) of plasma-depleted blood which was collected was calculated.

EXAMPLE 1

In this example, the membranes were 7 inches (178 mm) in diameter, and provided a total membrane surface area of about 0.05 m$^2$. A peripheral plasma-depleted blood collection channel, about 3.2 mm wide and 1.6 mm deep, surrounded the blood flow region of each plate. The membranes were adhered to circular plates, made from Du Pont Lucite ® acrylic resin, with a silicon adhesive which had a break elongation of 400%, a tensile strength of 350 psi (2.4 MPa), and a Shore A hardness of 30. The adhesive was applied by hand in a layer about 3 mils (76 μm) thick.

The same adhesive was used to form blood side supports by placing dots of the adhesive, between the membranes in two concentric circles. The blood flow path between the membranes was about 8 mils (0.20 mm) deep. The adhesive supports were cured on the blood side surface of one membrane at 60° C. overnight prior to assembly of the module. The plates were held together with clamps, without O-rings.

Blood having a hematocrit of 38% and being maintained at 37° C. was conducted forward by a 3-arm rotary peristaltic pump. A 0.33 psi (2.3×10$^3$ Pa) check valve was located between this pump and the blood reservoir.

Reciprocatory pulsations and pressure fluctuations were provided by a modified peristaltic pump, positioned on a loop, i.e., a length of tubing, which extended from two peripherally located ports and one centrally located port. The pump was modified so that a single roller, in constant contact with the tubing, oscillated in about a 50 mm stroke thereby displacing about 1.6 mL per stroke, at about 40 cycles-min$^{-1}$. A micrometer control valve was placed on the plasma-depleted blood outlet line and was adjusted during the treatment.

Results and conditions of this treatment are summarized in Table 1. Blood flow path pressure is reported in psi (kPa). Outlet Hct is the hematocrit, i.e., volume percent of red blood cells, of the plasma-depleted blood which was collected. No hemolysis was observed.

TABLE 1

| Elapsed Time (min) | Blood Inlet Flow Rate (mls.-min.$^{-1}$) | Blood Flow Path Pressure | | | | Plasma Flow Rate (mls.-min.$^{-1}$) | Outlet Hct. | Flux |
| --- | --- | --- | --- | --- | --- | --- | --- | --- |
| | | Peak | | Low | | | | |
| | | Inlet | Outlet | Inlet | Outlet | | | |
| 3.0 | 23.7 | 1.5 (10.3) | .6 (4.1) | −.8 (5.5) | −.6 (4.1) | 8.6 | 59.5 | .017 |

TABLE 1-continued

| Elapsed Time (min) | Blood Inlet Flow Rate (mls.-min.$^{-1}$) | Blood Flow Path Pressure | | | | Plasma Flow Rate (mls.-min.$^{-1}$) | Outlet Hct. | Flux |
|---|---|---|---|---|---|---|---|---|
| | | Peak | | Low | | | | |
| | | Inlet | Outlet | Inlet | Outlet | | | |
| 8.5 | 14.1 | 2.2 (15.2) | 2.0 (13.8) | −.4 (2.8) | −.1 (.7) | 8.2 | 90.1 | .016 |
| 12.5 | 15.7 | 3.0 (20.7) | 3.0 (20.7) | .5 (3.4) | .3 (2.1) | 8.8 | 86.3 | .018 |
| 17.0 | 15.4 | 3.0 (20.7) | 2.9 (20.0) | .8 (5.5) | .6 (4.1) | 8.2 | 81.1 | .016 |
| 22.0 | 14.6 | 2.7 (18.6) | 2.8 (19.3) | .6 (4.1) | .7 (4.8) | 8.4 | 88.9 | .017 |
| 25.5 | 15.1 | 3.6 (24.8) | 3.7 (25.5) | 1.9 (13.1) | 1.8 (12.4) | 8.5 | 86.6 | .017 |

EXAMPLE 2

The apparatus used in this example was identical to that described above in Example 1 except that the module was smaller, the membranes being about 6 inches (152 mm) in diameter and providing a total membrane surface area of about 0.04 m².

Results and conditions of this treatment are summarized in Table 2. No hemolysis was observed.

TABLE 2

| Elapsed Time (min) | Blood Inlet Flow Rate (mls.-min.$^{-1}$) | Blood Flow Path Pressure | | | | Plasma Flow Rate (mls.-min.$^{-1}$) | Outlet Hct. | Flux |
|---|---|---|---|---|---|---|---|---|
| | | Peak | | Low | | | | |
| | | Inlet | Outlet | Inlet | Outlet | | | |
| 3.0 | 22.1 | 2.0 (13.8) | .7 (4.8) | −1.2 (8.3) | −.8 (5.5) | 9.4 | 66.2 | .024 |
| 7.0 | 23.4 | 3.0 (20.7) | 2.0 (13.8) | −.3 (2.1) | 0 (0) | 12.3 | 80.3 | .030 |
| 12.5 | 10.2 | 3.4 (23.4) | 2.3 (15.9) | −1.0 (6.9) | −.2 (1.4) | 5.7 | 86.6 | .014 |
| 17.0 | 25.4 | 3.3 (22.8) | 2.5 (17.2) | .3 (2.1) | .5 (3.4) | 13.0 | 77.9 | .032 |
| 20.5 | 25.2 | 4.4 (30.3) | 3.9 (26.9) | 1.9 (13.1) | 2.2 (15.2) | 12.8 | 76.2 | .032 |

EXAMPLE 3

The apparatus used in this example was substantially identical to that described in Example 2. The inlet hematocrit was 37%. The stroke length of the oscillating pump was varied during the treatment. The oscillator was turned off for a three minute interval so that, during this period, blood was being conducted forward only. The inlet hematocrit was 37%.

Results and conditions of this treatment are summarized in Table 3. Slight hemolysis was briefly observed when the stroke length was changed from four inches (101 mm) to three inches (76 mm) and again when the oscillator was turned on after the one minute interval of constant flow.

transmembrane pressure difference in mm Hg (kPa), i.e. [(mean blood inlet pressure+mean plasma-depleted blood outlet pressure)÷2]−(mean plasma outlet pressure). Plasma flow rate is the rate at which plasma was collected in mL per minute. Hct is the hematocrit, i.e., volume percent of red blood cells, of the plasma-depleted blood which was collected.

EXAMPLE 4

Anticoagulated human blood, having a hematocrit of 32% and being maintained in a first reservoir at 37° C., was conducted into a plasmapheresis filtration module which is substantially depicted above by FIGS. 7, 11, 12 and 13. The module comprised six polycarbonate membranes, 10 μm thick, from Nuclepore Corporation, having 0.4 μm diameter pores. The total effective membrane surface area was 0.108 m². The height of the blood flow channels was 5 mils (0.13 mm). The module did not comprise a sealing envelope. The plates were clamped and then sealed around the perimeter with vacuum grease.

Reciprocatory pulsations were generated by a peristaltic pump on a loop comprised of two lengths of flexible tubing joining an inlet and an outlet. The pump was modified to oscillate with a 53 mm stroke length and a displacement of 7.5 mL.

Pressure transducers were located on the blood inlet line, the plasma line and the plasma-depleted blood outlet line. Plasma flowed into a vented level control chamber and was conducted from the chamber by a metering pump. Plasma and plasma-depleted blood were collected in a second reservoir and recycled to the first reservoir.

TABLE 3

| Elapsed Time (min) | Oscillator Stroke Length (mm) | Blood Inlet Flow Rate (mls.-min.$^{-1}$) | Blood Flow Path Pressure | | | | Plasma Flow Rate (mls.-min.$^{-1}$) | Outlet Hct. | Flux |
|---|---|---|---|---|---|---|---|---|---|
| | | | Peak | | Low | | | | |
| | | | Inlet | Outlet | Inlet | Outlet | | | |
| 1 | 101 | 51.3 | 3.2 (22.1) | 1.2 (8.3) | — | −1.0 (6.9) | 13.9 | 50.7 | .035 |
| 3.5 | 76 | 53.5 | 2.5 (17.2) | .7 (4.8) | −1.0 (6.9) | −.4 (2.8) | 14.7 | 51.0 | .037 |
| 7.0 | 76 | 53.8 | 2.9 (20.0) | 1.8 (12.4) | .1 (.7) | .3 (2.1) | 18.1 | 55.7 | .045 |
| 9.0 | 76 | 53.4 | 4.0 (27.6) | 3.5 (24.1) | 2.1 (14.5) | 2.1 (14.5) | 17.9 | 55.6 | .045 |
| 10.0 | 0 | 53.7 | 3.5 (24.1) | 3.5 (24.1) | 3.4 (23.4) | 3.4 (23.4) | 3.8 | 38.8 | .010 |
| 13.0 | 76 | 52.9 | 2.3 (15.9) | 1.5 (10.3) | .3 (2.1) | .5 (3.4) | 9.8 | 45.3 | .025 |
| 16.0 | 51 | 54.1 | 3.2 (22.1) | 2.6 (17.9) | 1.7 (11.7) | 1.7 (11.7) | 16.4 | 53.0 | .041 |

EXAMPLES 4 AND 5

Examples 4 and 5 are illustrative examples of plasmapheresis by reciprocatory pulsatile filtration using a module which is the invention of one other than the inventor herein.

The conditions and results of each example are tabulated. Pulse frequency is the frequency of reciprocatory pulsations in strokes per minute. Blood flow rate is the rate at which blood was conducted into the filtration module in mL per minute. STMP is the mean system Table 4 summarizes this example.

TABLE 4

| Time (min.) | Blood Flow Rate | Pulse Frequency | STMP | Plasma Flow Rate | Hct. |
|---|---|---|---|---|---|
| 5.0 | 53 | 30 | 14 (1.9) | 25.8 | 72 |
| 9.5 | 58 | 60 | 20 (2.7) | 21.2 | 80 |
| 13.5 | 76 | 30 | 30 (4.0) | 28.5 | 59 |
| 17.0 | 80 | 60 | 30 (4.0) | 37.6 | 60 |
| 20.5 | 100 | 30 | 32 (4.3) | 32.5 | 47 |
| 24.5 | 105 | 60 | 40 (5.3) | 39.5 | 51 |
| 32.0 | 135 | 30 | 44 (5.9) | 30.7 | 41 |
| 36.5 | 135 | 60 | 53 (7.1) | 36.8 | 44 |
| 40.0 | 170 | 30 | 53 (7.1) | 32.1 | 39 |
| 43.0 | 170 | 60 | 63 (8.4) | 37.6 | 41 |
| 46.0 | 200 | 30 | 61 (8.1) | 30.1 | 38 |
| 50.5 | 200 | 60 | 74 (9.9) | 36.6 | 39 |

This example was continued for a total of 92 minutes. Results from 50.5 to 92 minutes are not reported due to intermittent failure of the oscillator during this time period.

EXAMPLE 5

Anticoagulated human blood, having a hemotocrit of 38% and being maintained in a reservoir at 37° C., was conducted into a filtration module which is substantially depicted by FIGS. 7, 11, 12 and 13. The module comprised a single polycarbonate membrane, 10 μm thick, from Nuclepore Corporation, having 0.6 μm diameter pores. The effective membrane surface area was 0.018 m². The height of the blood flow channels was 4.5 mils (0.11 mm). The module did not comprise a sealing envelope. The plates were clamped and then sealed around the perimeter with vacuum grease.

Reciprocatory pulsations were generated in similar fashion to Example 4. The stroke length was 53 mm and the displacement was 0.42 mL.

Pressure transducers were located on the blood inlet line and the plasma-depleted blood outlet line. Plasma pressure was assumed to be atmospheric. Plasma and plasma-depleted blood were not recycled.

Table 5 summarizes this example.

TABLE 5

| Blood Flow Rate | Pulse Frequency | STMP | Plasma Flow Rate | Hct. |
|---|---|---|---|---|
| 9.5 | 42 | 62 (8.3) | 4.5 | 72 |
| 10.6 | 42 | 98 (13.1) | 4.9 | 70 |
| 20.0 | 42 | 16 (2.1) | 3.5 | 46 |
| 20.4 | 42 | 70 (9.3) | 7.0 | 58 |
| 9.4 | 42 | 67 (8.9) | 4.4 | 71 |
| 9.1 | 20 | 70 (9.3) | 3.0 | 57 |
| 9.9 | 60 | 54 (7.2) | 4.8 | 74 |

Conditions and results are reported at approximately 4 to 6 minute intervals.

BEST MODE

The best mode for carrying out the invention is illustrated generally by FIGS. 4 through 10.

While the preferred embodiments of the invention are illustrated and described above, it is to be understood that the invention is not limited to the precise constructions herein disclosed and that the right to all changes and modifications coming within the scope of the following claims is reserved.

I claim:

1. In a plasmapheresis wherein whole blood is conducted in a forward direction from an upstream area of a first surface of each of one or more membranes having cell-rejecting pores to a downstream area of the first surface, plasma-depleted blood is collected from the downstream area of the first surface, and plasma is separately collected from a second surface of each of the one or more membranes, the plasmapheresis being carried out in a system closed off from the atmosphere by:

(a) while maintaining a net positive transmembrane pressure difference across the membrane, conducting plasma-depleted blood in the reverse direction over the first surface by delivering collected plasma-depleted blood to the downstream area of the first surface and reducing the transmembrane pressure difference across the membrae in the upstream area whereat whole blood is introduced to ≦0 by either withdrawing and collecting blood from the upstream area of the first surface or increasing the pressure on a second surface of the one or more membranes, while collecting blood from the upstream area of the first surface, so that blood in the upstream area of the first surface is at a pressure which is not only lower than the downstream plasma-depleted blood pressure but also lower than the pressure on the second surface;

(b) terminating the reverse conducting of step (a);

(c) while maintaining the net positive transmembrane pressure difference across the membrane, conducting whole blood in the forward direction over the first surface by delivering collected blood from step (a) to the upstream area of the first surface and reducing the transmembrane pressure difference across the membrane in the downstream area whereat plasma-depleted blood is collected to ≦0 by either withdrawing and collecting plasma-depleted blood from the downstream area of the first surface or increasing the pressure on a second surface of the one or more membranes, while collecting plasma-depleted blood from the downstream area of the first surface, so that plasma-depleted blood in the downstream area of the first surface is at a pressure which is not only lower than the upstream blood pressure but also lower than the pressure on the second surface; and (d) repeating steps (a) to (c) in sequence, said plasmapheresis further characterized in that blood is oscillated in an external loop between the upstream area and the downstream area of the first surface.

2. Plasmapheresis of claim 1 which comprises superimposing oscillatory flow on a continuous forward flow of the blood.

3. Plasmapheresis of claim 2 which comprises oscillating about 0.5 to about 4 mL of blood at a rate of 20 to 140 cycles-min$^{-1}$.

4. Plasmapheresis of claim 2 which comprises oscillating blood in a flow path on a surface of each of a plurality of membranes each having cell-retaining pores, 0.1 to 1.0 μm in average diameter.

5. Plasmapheresis of claim 4 which comprises oscillating the blood in a circuit which includes the flow path and a loop extending between an inlet and an outlet of the flow path.

6. Plasmapheresis of claim 5 which comprises oscillating blood in a flow path between two polycarbonate or polyester planar membranes, each being supported on the plasma sides, at a blood flow path depth of at least 4 mils (102 μm).

7. Plasmapheresis of claim 4, 5 or 6 which comprises oscillating blood at a velocity up to about 400 mm per second.

8. Plasmapheresis of claim 7 which comprises oscillating blood at a rate of 20 to 140 cycles-$\text{min}^{-1}$ at a depth of about 4 to 10 mils (102 to 254 μm) and at a velocity up to about 250 mm per second.

9. Apparatus for continuously separating plasma from blood without substantial hemolysis, which apparatus comprises one or more membranes having cell-rejecting pores, inlet means for introducing blood to a first surface of a membrane, outlet means for removing blood from a first surface of a membrane, means for conducting blood forward at a net positive transmembrane pressure difference and reverse over a first surface of each membrane, means for reducing the transmembrane pressure difference during the forward and reverse conducting of blood, means for collecting plasma which passes through each membrane from a second surface thereof, means for withdrawing and collecting blood from said first surface, means for withdrawing and collecting plasma-depleted blood from said first surface, means for delivering collected blood to said first surface, means for delivering collected plamsa-depleted blood to said first surface and means for operating the apparatus closed off from the atmosphere, said apparatus further characterized in that it includes external means for oscillating blood between the inlet means and the outlet means.

10. Apparatus of claim 9 which comprises means for superimposing oscillatory flow on a continuous forward flow of the blood.

11. Apparatus of claim 10 which comprises means for oscillating about 0.05 to about 4 mL of blood at a rate of 20 to 140 cycles-$\text{min}^{-1}$.

12. Apparatus of claim 10 comprising a plurality of membranes each having cell-retaining pores, 0.1 to 1.0 μm in average diameter.

13. Apparatus of claim 12 in which the means for oscillating the blood comprises a circuit which includes the flow path and a loop extending between an inlet and an outlet of the flow path, the loop being provided with oscillating means.

14. Apparatus of claim 13 in which the blood flow path is between two polycarbonate or polyester planar membranes, each having a plasma side support, the depth of the blood flow path being at least 4 mils (102 μm).

15. Apparatus of claim 12, 13 or 14 which comprises means for oscillating blood at a velocity up to about 400 mm per second.

16. Module of claim 15 which comprises means for oscillating blood at a rate of 20 to 140 cycles-$\text{min}^{-1}$ at a depth of about 4 to 10 mils (102 to 254 μm) and at a velocity up to about 250 mm per second.

* * * * *